United States Patent [19]

Hanover et al.

[11] Patent Number: 5,059,175
[45] Date of Patent: Oct. 22, 1991

[54] IMPLANTABLE DRUG DELIVERY SYSTEM WITH PISTON ACTUATION

[75] Inventors: Barry K. Hanover; Stephen C. Jacobsen; Eric M. Simon; Tomasz Petelenz, all of Salt Lake City; Michael G. Mladejovsky, Murray, all of Utah

[73] Assignee: University of Utah Research Foundation, Salt Lake City, Utah

[21] Appl. No.: 594,271

[22] Filed: Oct. 9, 1990

[51] Int. Cl.⁵ .............................................. A61K 9/22
[52] U.S. Cl. ................................ 604/891.1; 604/890.1
[58] Field of Search ................... 604/285, 246, 890.1, 604/891.1, 892.1, 140, 141, 143, 145

[56] References Cited

U.S. PATENT DOCUMENTS 3,923,060 12/1975 Ellinwood, Jr. .
4,140,122 2/1979 Kühl et al. .
4,411,651 10/1983 Schulman .

Primary Examiner—Randall L. Green
Assistant Examiner—Trinh Nguyen
Attorney, Agent, or Firm—Thorpe North & Western

[57] ABSTRACT

An implantable drug delivery system includes a housing having a base end and a discharge end, for holding drug solution at the discharge end, a valve disposed at the discharge end to allow a drug solution to flow from inside the housing, through the valve and out of the housing when solution pressure is applied to the valve, a piston slidably disposed in the housing to slide between the base end and discharge end to force solution toward the discharge end and out the valve, and a spring disposed in the housing between the piston and the base end thereof for urging the piston toward the discharge end. A plurality of different length tethers are connected at one end to the piston and at the other end to a respective release node located at the base end of the housing. Each release node holds the other end of a respective one of the tethers until a release signal is received at which time it releases the tether. A timing circuit is disposed in the housing at the base end to supply release signals sequentially to the nodes in order of the shortest tether node to the longest tether node so that as a tether is released, the piston is allowed to move toward the discharge end of the housing to thereby discharge or bolus of drug solution from the housing, until the next shortest unreleased tether stops further movement of the piston.

14 Claims, 2 Drawing Sheets

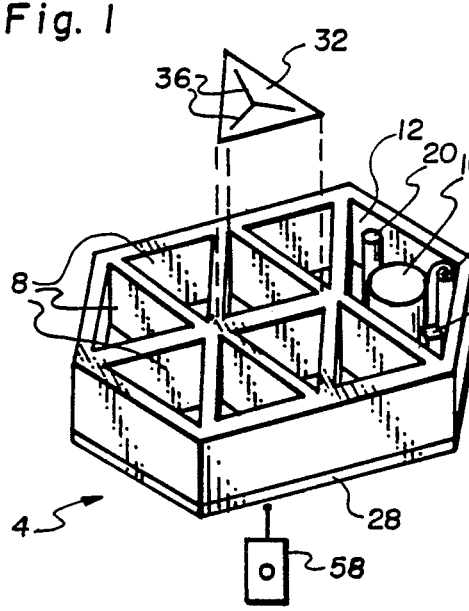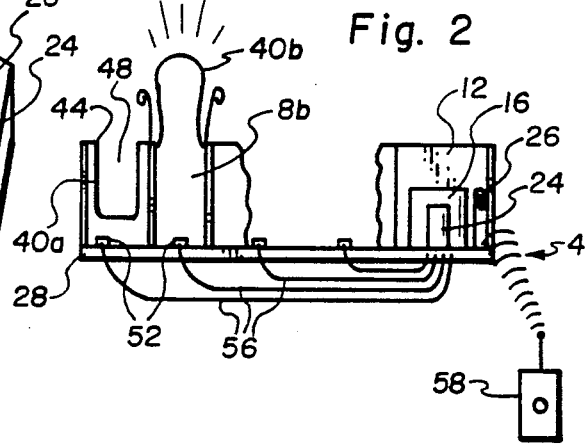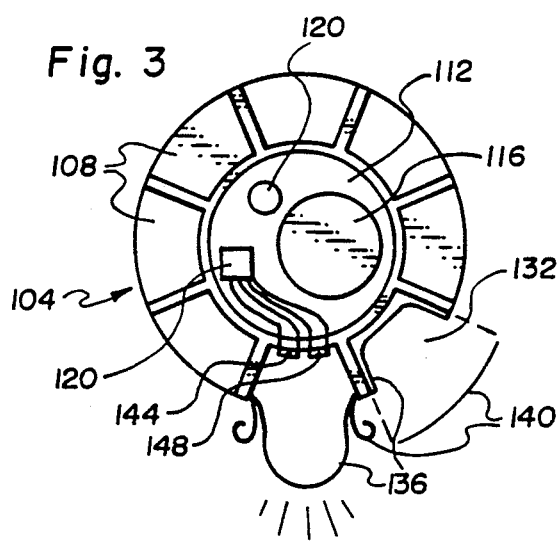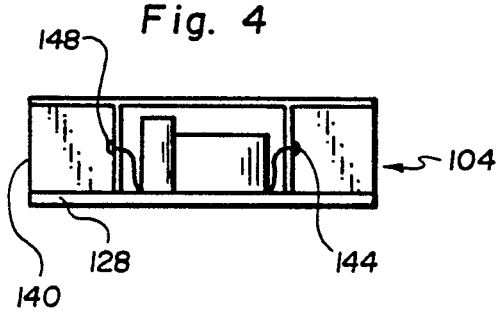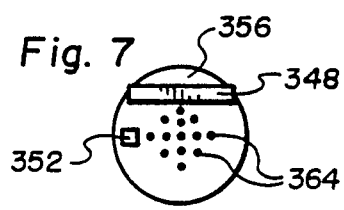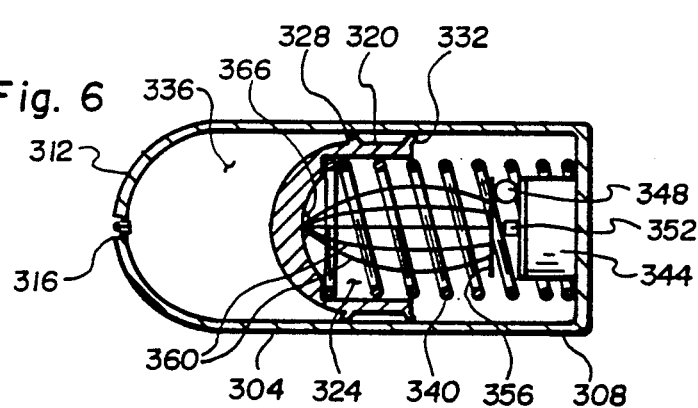

IMPLANTABLE DRUG DELIVERY SYSTEM WITH PISTON ACTUATION

BACKGROUND OF THE INVENTION

The present invention relates to simple and efficient piston-actuated drug delivery systems for implantation into an animal or human for delivery of drug to the animal or human incrementally over some period of time.

It is well known in the fields of animal husbandry and veterinary medicine that it is desirable and in some instances necessary to treat or care for farm animals by periodically injecting the animals (or administering orally) with various drugs. If a series of injections or other administrations are required, this may require finding and rounding up the animals, administering the desired drug (or different drugs), and then releasing the animals until the next drug administration is due. Of course, it can be time consuming and costly, each time treatment of a farm animal is required, to locate the farm animal and bring it to a suitable location for treatment. It has been proposed that drug delivery devices be implanted in farm animals for the periodic release of drugs, examples of such devices being disclosed in U.S. Pat. Nos. 4,564,363, 4,326,522, 4,425,117, 4,439,197, 3,840,009, 4,312,347 and 4,457,752.

Although the devices disclosed in the above-cited patents serve to deliver a drug or solution to the body of an animal or person in which they are located, the devices are typically limited to specific applications, allow for a one-time discharge (a continuous delivery) of drug into the system of the body in which the device is located, are bulky and therefore difficult to place and maintain in the body, or are complicated and costly to manufacture and use.

SUMMARY OF THE INVENTION

It is an object of the invention to provide a simple and efficient drug delivery system which may be implanted in the body of an animal or human for timed, periodic release of the drug into the body.

It is also an object of the invention to provide such a drug delivery system which is compact and can be readily manufactured.

It is a further object of the invention to provide such a drug delivery system which has a high ratio of drug volume to housing or package volume.

It is an additional object of the invention to provide such a drug delivery system which is reliable and substantially leak free.

The above and other objects of the invention are realized in a specific illustrative embodiment of an implantable drug delivery system which includes a housing having a base end and a discharge end, for holding drug formulation at the discharge end, a one-way valve disposed at the discharge end to allow formulation to flow or move through the valve and out of the housing when formulation pressure is applied to the valve, a piston slidably disposed in the housing to slide between the base end and discharge end to force formulation toward the discharge end and out the valve, and a biasing element for urging the piston toward the discharge end of the housing. Also included is a restraining member for allowing successive step-wise movement of the piston toward the discharge end of the housing in response to release signals, but for otherwise restraining movement of the piston. A control unit located at the base end of the housing supplies release signals to the restraining member in a predetermined sequence so that drug formulation is successively forced out of the housing in discreet amounts.

BRIEF DESCRIPTION OF THE DRAWINGS

The above and other objects, features and advantages of the invention will become apparent from a consideration of the following detailed description presented in connection with the accompanying drawings in which:

FIG. 1 is a perspective view of an implantable drug delivery multiple-vesicle device made in accordance with the principles of the present invention;

FIG. 2 is a side, fragmented, cross-sectional view of the device of FIG. 1;

FIG. 3 is a top, plan, cross-sectional view of another embodiment of a multiple-vesicle drug delivery system made in accordance with the principles of the present invention;

FIG. 4 is a side view of the embodiment of FIG. 3 but showing only a few of the component parts;

FIG. 6 is a side, cross-sectional view of still another embodiment of a drug delivery system made in accordance with the principles of the present invention and utilizing a plunger in a single cylindrical vesicle;

FIG. 7 is a top, plan view of the release mechanism of FIG. 6;

DETAILED DESCRIPTION

Figure 5:
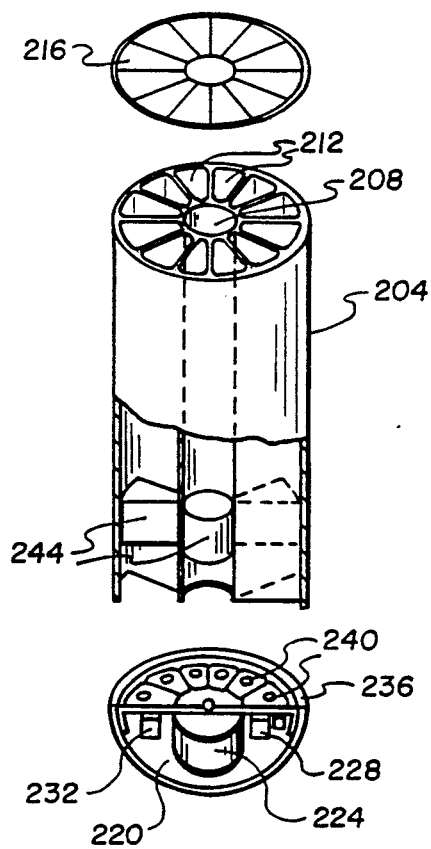
FIG. 5 is an isometric, exploded, partially cutaway view of still another embodiment of a drug delivery system made in accordance with the principles of the present invention and utilizing piston or plunger discharge elements in multiple vesicles.

Referring to FIGS. 1 and 2 of the drawings, there is shown a low profile, compact drug delivery system made in accordance with the present invention to include a housing 4 having formed therein two (or more) rows of vesicles or compartments 8, each having top, polygonally shaped cross-sections to allow compact nesting together of the compartments. The compartments shown in the FIGS. 1 and 2 embodiment have triangular top cross sections, but other shapes could also be used to achieve the desired nesting.

Positioned at one end of the two rows of compartments 8 is a utility compartment 12 in which is housed a battery 16, an oscillator 20, a timing circuit 24, and a receiver and antenna 26. The elements 16, 20, 24 and 26 are mounted on a substrate 28 which forms the floor of the utility compartment 12 and the other compartments 8.

Each compartment 8 has an opening at the top which is covered by a rupturable cover, such as the one cover 32 shown. The covers 32 might illustratively be made of a thin metal foil or might be made of a thin plastic sheet. Score lines 36 may be formed in the cover 32 to more readily facilitate the rupture of the cover and the release of the contents of the corresponding compartment (to be discussed momentarily). The housing 4 might advantageously be made of injection molded polycarbonate or other plastics. The substrate 28 might illustratively be made of conventional circuit board material such as a fiberglass and epoxy composite or polyamide film, for carrying the circuit component 16, 20, 24 and 26 and electrical conductors to be discussed later.

Disposed in each compartment 8 is a corresponding drug containment sack 40 having a mouth 44 which circumscribes an opening 48 to the interior of the sack (see FIG. 2). The mouth 44 of each drug containment sack is attached to the opening of the corresponding compartment, at the top thereof, to seal the inside of each sack from the inside of the corresponding compartment. The drug containment sacks are provided for holding drug solution (or powder or granular formulation) to be delivered to an animal into which the drug delivery system is implanted. The sacks 40 might illustratively be made of polyvinylidene chloride, fluorinated ethylene-propylene, or other suitably flexible and fluid and chemical impervious material.

Disposed at the bottom of each compartment on the substrate 28 is a pyrotechnic gas generating element, typically a bead of material 52 which is responsive to heat resulting from an electrical signal applied to a heating element, thereby igniting and producing gas for filling the corresponding compartment. Alternatively, a non-toxic foam may be produced by an ignition material to similarly fill a corresponding compartment. As a compartment fills with gas, the gas forces the corresponding drug containment sack upwardly and the sack, in turn, forces drug solution against a corresponding cover 32 to rupture the cover and allow the drug solution and sack to be emitted from the compartment. Sack 40b of FIG. 2 is shown fully pushed out of the compartment 8b which ensures that all drug solution initially contained in the sack is released into the animal.

The pyrotechnic gas generating material 52 might illustratively be a composition of nitrocellulose or polyvinyl nitrate. Although not shown, a second pyrotechnic gas generating bead might also be included in each compartment to be activated after the first bead has been activated to thereby better ensure the complete release of drug solution from each compartment.

The timing circuit 24 operates in response to a remotely transmitted signal (transmitted by a transmitter 58) received by the receiver and antenna 26 to selectively and sequentially connect the battery 16 by way of electrical conductors 56 to the pyrotechnic gas generating beads 52. Remotely transmitted signals could be used simply to initiate operation of the timing circuit 24 which would then periodically activate selected gas generating beads 52 on its own, or the transmitted signals could be used to directly activate a bead with each transmitted signal. (Although the conductors 56 are shown as being under the substrate 28 in FIG. 2, this is for illustrative purposes only and it should be understood that the conductors would be formed upon the substrate by conventional photo-lithographic, vacuum deposition, or other conventional conductor forming techniques.) The conductors 56 could illustratively be made of a relatively low resistance conductive ink made, for example, of a resin and carbon and silver particles. An alternative to initiating operation of the timing circuit 24 by radio or other signal transmission would be simply to internally set the timing circuit to begin operation some predetermined time in the future—e.g., after supplying the drug delivery system to an animal.

The oscillator 20 supplies an oscillatory signal to the timing circuit 24 which is adapted to selectively connect the battery 16 to the pyrotechnic gas generating beads 52 in some preferred order (to activate the beads) and with a predetermined delay between activation of the different beads, to thereby discharge boluses of drug solution into the animal over a period of time.

FIGS. 3 and 4 show another embodiment of a drug delivery system having a short, cylindrically-shaped housing 104 having a plurality of compartments 108 formed in a circle about a central utility compartment 112. The utility compartment 112 again includes a battery 116, an oscillator 120 and a timing circuit 124, all mounted on a substrate 128 which forms a common floor for the utility compartment 112 and the other compartments 108. (A receiver and antenna could also be provided for this embodiment as well as the other embodiments, for remote operation, as explained for the FIGS. 1 and 2 embodiment.)

Although the compartments 108 could have openings at the top of the housing 104, similar to the embodiment of FIGS. 1 and 2, the compartments are shown as having openings 132 in the circumferential outer wall of the housing. Drug containment sacks 136 are disposed in each compartment for holding a drug solution, and rupturable covers 140 are disposed over the compartment openings as best seen in FIG. 3. Alternatively to placing individual covers 140 over each of the compartment openings, a single strip cover could be disposed at the circumferential outer side of the housing 104 to cover all of the openings, with appropriate scoring of the cover being made to allow release of drug solution only from those compartments which are activated. A pair of individually activatable pyrotechnic gas generating beads 144 and 148 (FIG. 3) are disposed in each compartment on the wall opposite the compartment opening (or on the substrate floor), for producing gas to discharge the contents of the compartment in response to an electrical ignition signal.

FIG. 5 shows an isometric, exploded, partially cutaway view of a drug delivery system having an elongate, tubular housing 204. Formed in the housing is a central compartment or vesicle 208, and a plurality of other vesicles 212 disposed in a circle about the central vesicle as shown. The vesicles extend along a substantial length of the housing 204 generally in parallel with one another and include openings at the upper end of the housing. A rupturable cover 216 is disposed over the upper end of the housing to cover the openings of the vesicles, but to also rupture and allow discharge of the contents of a vesicle when a certain fluid pressure is supplied to the cover from inside the vesicle. Although the vesicles 212 are shown to be generally the same size, different size vesicles could be provided to allow for delivery of different amounts of drug—both of this embodiment and the others.

The housing 204 also includes a bottom compartment 220 in which are disposed a battery 224, an oscillator 228 and a timing circuit 232. The compartment 220 is separated from the vesicles 208 and 212 by a floor or substrate 236 in which are located a plurality of pyrotechnic gas generating beads 240. The circuit components 224, 228 and 232 selectively and successively ignite the pyrotechnic gas generating beads 240 in the same manner as discussed for the embodiments of FIGS. 1 and 2 and FIGS. 3 and 4.

Disposed in each vesicle 208 and 212 near the bottoms thereof are pistons or plungers 244. The side surfaces of the plungers 244 are shaped to conform to and snugly fit within the side walls of the corresponding vesicles so that as a plunger is forced upwardly in a vesicle by gas pressure, it pushes out of the housing a drug formulation contained in the vesicle. The plungers 244 are forced upwardly in the corresponding vesicles by the activation of the pyrotechnic gas generating beads (or other geometric shapes) 240.

Advantageously, the plungers 244 are made of polyurethane, synthetic rubber or paraffin which will allow for a slidably tight fit within the vesicles and will also provide some lubrication to facilitate the sliding of the plungers. The housing 204 could illustratively be made of injection molded polycarbonate.

FIGS. 6 and 7 show respectively a side, cross-sectional view of another embodiment of an implantable drug delivery system, and a top plan view of the release mechanism of the system. The FIGS. 6 and 7 system include a housing 304 having a base end 308 and a discharge end 312. A passive one-way valve 316 is disposed in the discharge end of the housing to allow release of drug formulation contained in the housing when a certain fluid pressure is applied from inside the housing to the valve.

Disposed in the housing is a piston or plunger 320 having a spring receiving hollow 324 on the underneath side thereof. The exterior side wall of the plunger 320 includes axially spaced apart wipers or seals 328 and 332 for making intimate but slidable contact with the interior side wall of the housing 304. The plunger 320 is positioned in the housing 304 initially at a location to define a cavity or reservoir 336 above the plunger for holding a drug formulation.

Also disposed in the housing 304 is a coil spring 340 which extends from a bottom wall at the base end of the housing 308 upwardly into the hollow 324 of the plunger 320. A battery 344, oscillator 348 and timing circuit 352 are disposed within the coil spring 340 on the bottom wall of the housing (but could also be disposed in the plunger 320). Disposed above the circuit elements 344, 348 and 352 is a release circuit card 356 (a bottom view being shown in FIG. 7 with the oscillator 348 and timing circuit 352 mounted thereon).

A plurality of different length tethers or fibers 360 are attached at one end to the underside of the plunger 320 and at the other end to release nodes 364 disposed on the circuit card 356. The tethers 360 serve to hold the plunger in place and prevent it from being moved upwardly toward the discharge end of the housing by the spring 340 until selected tethers are released from the circuit cards. In particular, each of the tethers, being a different length, serve to hold or retain the plunger 320 at different distances away from the circuit card 356 until the tether holding the plunger at a respective length is released from its corresponding release node 364. In this manner, the tethers 360 can be successively released to allow a stepwise movement upwardly of the plunger 320 to successively discharge boluses of drug formulation contained in the reservoir 336.

The release nodes 364 are composed of a material (e.g., ultra-high-modulus polyethylene) capable of holding the ends of the respective tethers 360 until the material is activated or ignited in response to an electrical signal to either sever or release the corresponding tether end. Each release node 364 is coupled to the timing circuit 352 which selectively supplies an electrical release signal from the battery 344 to the nodes. Release signals are supplied to the release nodes 364 in the order of increasing tether length so that the shortest tether is first released to allow the plunger 320 to move upwardly one increment, the next shortest tether is then released, etc. until the plunger has been forced by the spring 340 to the top of the housing 304 at the discharge end.

In the event that any tether 360 is not released, then any subsequent release node 364 activated by the timing circuit 352 will not be able to allow any further movement of the plunger 320. Nevertheless, a completion release node 366, located at the point of connection of the tethers 360 to the plunger 320, may be activated to sever or release all tethers to allow a final thrust of the plunger 320 toward the discharge end 312 of the housing. In this manner, even though one of the tethers 360 may have failed to release, activation of the release node 366 would provide for the release of all the tethers and a final movement of the plunger 320.

Figure 8:
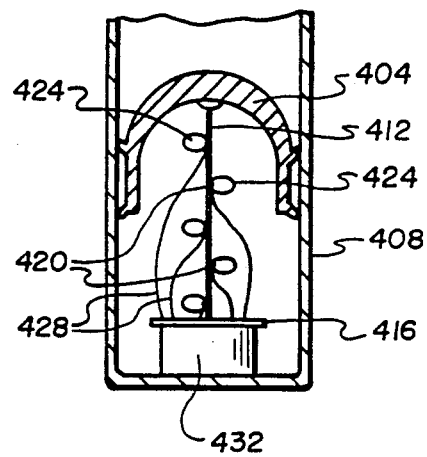
FIG. 8 is a fragmented, side, cross-sectional view of another embodiment of a drug delivery system made in accordance with the principles of the present invention.

FIG. 8 shows a fragmented, side, cross-sectional view of another embodiment of a drug delivery system which also utilizes a plunger 404 slidably disposed in a housing 408. A coil spring, not shown but similar to the spring 340 of the system of FIG. 6, is also disposed in the housing 408 to bias or urge the plunger 404 upwardly toward a discharge end of the housing.

The plunger 404 is prevented from its upward movement by a single tether 412 coupled at one end to the plunger 404 and at the other end to a circuit card 416. Successive pairs of points along the length of the tether 412 are joined together by release elements 420 to thus form a series of loops 424 in the tether. The release elements join the two corresponding points of the tether 412 together until activated by release signals supplied by way of conductors 428 by a circuit pack 432. As a release element 420 is activated, the two adjacent points of the tether 412 joined together are released so that the effective length of the tether increases to allow an upward movement of the plunger 404. As a next release element is activated, another loop of the tether is released so that the tether again increases its effective length to allow another upward movement of the plunger 404. In this manner, by successive application of release signals to the release elements 420, the plunger 404 is allowed successive upward movements to thereby force drug solution located above the plunger to discharge out the discharge end of the housing 408.

Figure 9:
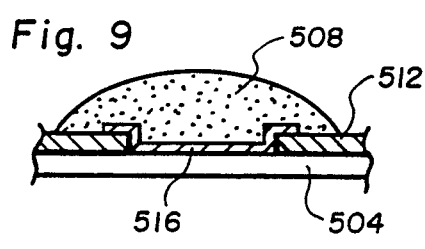
FIG. 9 is a side, elevational view of one embodiment of a pyrotechnic gas generating element made in accordance with the present invention.
Figure 10:
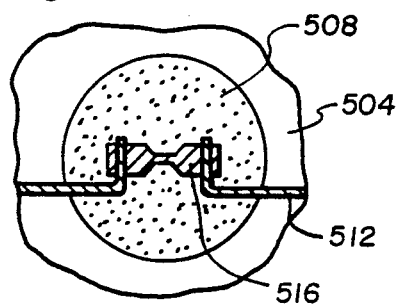
FIG. 10 is a top plan view of the embodiment of FIG. 9.

FIGS. 9 and 10 show a side, elevational, partially cross-sectional view and a top plan view respectively of a pyrotechnic gas generating element suitable for use in the embodiments of FIGS. 1 through 5 of the drawings. The element is disposed on a substrate or base 504 to include a pyrotechnic material 508 which ignites easily and burns in response to an electrical signal supplied over lead 512 to an igniter strip 516. Such pyrotechnic material might advantageously be composed of nitrocellulose, barium styphnate or tetrazene. The igniter strip 516 might illustratively be made of nickel chromium. Lead 512 might illustratively be copper, copper alloy or gold. The burning of the pyrotechnic material produces gas as required for forcing drug formulation from vesicles of drug delivery apparatus.

To actuate the gas generating element of FIGS. 9 and 10, an electrical signal is supplied to the conductor 512 to flow through the igniter strip 516 causing it to heat and combust the pyrotechnic material 508.

Figure 11:
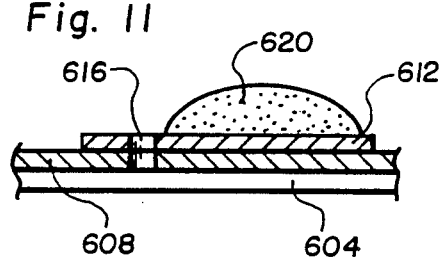
FIG. 11 is a side, elevational view of another embodiment of a pyrotechnic gas generating element made in accordance with the present invention.
Figure 12:
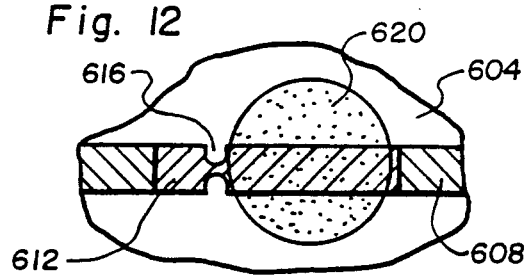
FIG. 12 is a top plan view of the embodiment of FIG. 11.

FIGS. 11 and 12 show a side, elevational view and top plan view of another pyrotechnic gas generating element which may be used in the drug delivery apparatus of FIGS. 1-5. The element is disposed on a substrate 604 which includes an electrical conductor 608 formed of aluminum. Disposed on the aluminum strip 608 is a strip of a composition 612 of palladium (about 95 percent) and ruthenium (about 5 percent) which is narrowed or pinched at 616. Disposed over and about the composition 612 is a mass of pyrotechnic material 620 as discussed earlier.

When an electrical signal is supplied to the conductor 608 and to the composition 612, the composition alloys—heats exothermally—and this reaction progresses under the pyrotechnic material to ignite it and thus produce the desired gas. The narrowed portion 616 presents greater resistance to the electrical signal to start the alloying process.

In the manner described, simple, compact drug delivery units may be provided for implantation into an animal to release successive, timed bursts of drug solution. The volume of each unit utilized for drug containment is high relative to the volumes used for containing circuitry or other elements of the units.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed:

1. An implantable drug delivery system comprising
an elongate housing having a plurality of elongate, generally parallel vesicles formed therein, said vesicles having an opening at one end and a bottom wall at the other end,
a plurality of plungers, each disposed in a different one of the vesicles and shaped to fit and slide snugly in the corresponding vesicle, said plungers initially positioned near the bottom walls of the vesicles to allow reception and holding of drug formulation in the vesicles above the plungers,
a plurality of caps, each removably positioned over a respective opening of a vesicle to prevent release of drug formulation from the vesicles, said caps being releasable to release drug formulation when formulation is forced against the caps by the upward movement of the plungers,
a plurality of gas generating means, each disposed at the bottom wall of a different one of the vesicles and each being responsive to an ignition signal for igniting to generate gas and force a corresponding plunger upwardly to push drug formulation against a corresponding cap and out the vesicle, and
means for selectively supplying ignition signals to said gas generating means.

2. A system as in claim 1 wherein said ignition signal supplying means is disposed in the housing below the bottom walls of the vesicles.

3. A system as in claim 2 wherein one of said vesicles is positioned centrally with the other vesicles positioned circumferentially about the one vesicle.

4. A system as in claim 2 wherein said plungers are composed of material selected from the group consisting of polyurethane, synthetic rubber, and paraffin.

5. A system as in claim 2 wherein said caps are made of thin metallic foil.

6. A system as in claim 2 wherein said caps are made of a polymeric sheet.

7. A system as in claim 2 wherein said housing comprises an integral, unitary structure.

8. A system as in claim 6 wherein said housing is constructed of injection molded polycarbonate.

9. A system as in claim 2 wherein each of said gas generating means comprises a pyrotechnic composition of a gas generating material responsive to heat for further heating and producing gas, a heating element disposed in contact with the composition for heating in response to an electrical signal, and wherein said ignition signals comprise electrical signals.

10. A system as in claim 9 wherein said heating element comprises a strip of nickel chromium, and wherein said composition is disposed over the strip.

11. A system as in claim 9 wherein said heating element comprises a composition of palladium and rethenium disposed in contact with aluminum.

12. A system as in claim 9 wherein said ignition signal supplying means comprises
a power source, and
a switching circuit for operating to selectively temporarily couple the power source to the heating elements in a predetermined sequence.

13. A system as in claim 12 wherein said signal supplying means comprises conductors for carrying electrical signals from the power source to the heating elements.

14. A system as in claim 12 wherein said ignition signal supplying means further comprises means for receiving an externally transmitted signal for initiating operation of the switching circuit.

* * * * *